United States Patent
Wyllie, II et al.

(10) Patent No.: US 8,267,686 B2
(45) Date of Patent: Sep. 18, 2012

(54) ORTHODONTIC BRACKET WITH BRAZED ARCHWIRE SLOT LINER

(75) Inventors: William E. Wyllie, II, Pasadena, CA (US); John J. Palmer, Monrovia, CA (US); Glenys A. Thorstenson, Azusa, CA (US); David S. Arney, St. Paul, MN (US); John S. Kelly, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 1044 days.

(21) Appl. No.: 11/536,724

(22) Filed: Sep. 29, 2006

(65) Prior Publication Data

US 2008/0081309 A1 Apr. 3, 2008

(51) Int. Cl.
*A61C 3/00* (2006.01)
(52) U.S. Cl. .......................................... 433/8
(58) Field of Classification Search ................ 433/8–17, 433/22, 207; 228/262.42, 262.61, 262.9
See application file for complete search history.

(56) References Cited

U.S. PATENT DOCUMENTS

| 4,883,745 A * | 11/1989 | Mizuhara ...................... 420/502 |
| 4,954,080 A | 9/1990 | Kelly et al. |
| 5,095,602 A | 3/1992 | Reher et al. |
| 5,154,606 A | 10/1992 | Wildman |
| 5,314,109 A | 5/1994 | Farzin-Nia |
| 5,330,098 A * | 7/1994 | Mizuhara ...................... 228/214 |
| 5,358,402 A * | 10/1994 | Reed et al. ......................... 433/8 |
| 5,358,796 A | 10/1994 | Nakamura et al. |
| 5,368,661 A | 11/1994 | Nakamura et al. |
| 5,380,196 A | 1/1995 | Kelly et al. |
| 5,424,140 A | 6/1995 | Rabinkin |
| 6,257,882 B1 | 7/2001 | Wyllie, II |
| 6,302,688 B1 | 10/2001 | Jordan et al. |
| 6,582,226 B2 | 6/2003 | Jordan et al. |
| 6,648,638 B2 * | 11/2003 | Castro et al. ..................... 433/8 |
| 6,743,013 B2 | 6/2004 | Jordan et al. |
| 6,913,459 B2 * | 7/2005 | Fukutomi ......................... 433/8 |
| 7,014,460 B2 | 3/2006 | Lai et al. |
| 7,140,875 B2 | 11/2006 | Lai et al. |
| 7,192,274 B2 | 3/2007 | Stadtmiller et al. |
| 2005/0123875 A1 | 6/2005 | Stadtmiller et al. |

OTHER PUBLICATIONS

M. Holt, et al., "Fracture resistance of ceramic brackets during arch wire torsion," from *Amer. J. of Orthodontics and Dentofacial Orthopedics*, vol. 99, No. 4, Apr. 1991, pp. 287-293.

* cited by examiner

*Primary Examiner* — Sunil K Singh
(74) *Attorney, Agent, or Firm* — Philip P. Soo

(57) ABSTRACT

An orthodontic article and method of making the orthodontic article, where the orthodontic article includes a fine-grain ceramic bracket and a metal liner secured in an archwire slot of the bracket with a brazing alloy comprising silver, copper, and at least about 1.5% by weight titanium.

20 Claims, 3 Drawing Sheets

ORTHODONTIC BRACKET WITH BRAZED ARCHWIRE SLOT LINER

BACKGROUND OF THE INVENTION

The present invention relates to dental articles for use in orthodontic treatments to correct malocclusions. In particular, the present invention relates to ceramic orthodontic brackets having brazed archwire slot liners for receiving archwires.

Orthodontic treatment is directed to the movement of teeth to improved positions for enhancing a patient's facial appearance, especially in areas near the front of the patient's mouth. Orthodontic treatment may also improve the patient's occlusion so that the teeth function better with each other during mastication.

One type of orthodontic treatment system includes a set of brackets, which are fixed to the patient's anterior, cuspid, and bicuspid teeth. Each of the brackets has an archwire slot to receive a resilient archwire. The archwire functions as a track to guide movement of the brackets, and hence movement of the associated teeth, to desired positions. Ends of the archwire are typically received in passages of small appliances known as buccal tubes that are fixed to the patient's molar teeth.

Orthodontic brackets are available in a variety of materials, such as metallic materials, plastic materials, and ceramic materials. Ceramic materials are particularly popular because they may provide brackets that are transparent or translucent. The transparent or translucent appearance reduces the visibility of the brackets, thereby preserving aesthetic qualities. Archwire slot liners are typically used with ceramic-material brackets because the metal-to-metal contact between the archwires and the liners provide better sliding mechanics compared to the metal-to-ceramic material contact between the archwires and the brackets. However, archwire slot liners require secure bonds to the brackets during use to prevent the archwire slot liners from separating from the brackets. As such, there is a need for bonding systems that provide strong bonds between archwire slot liners and orthodontic brackets.

BRIEF SUMMARY OF THE INVENTION

The present invention relates to an orthodontic article and method of making the orthodontic article. The orthodontic article includes a bracket derived from a fine-grain ceramic material, and a metal liner secured within an archwire slot of the bracket with a silver-copper-titanium (Ag—Cu—Ti) brazing alloy that includes at least about 1.5% by weight titanium.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Figure 1:
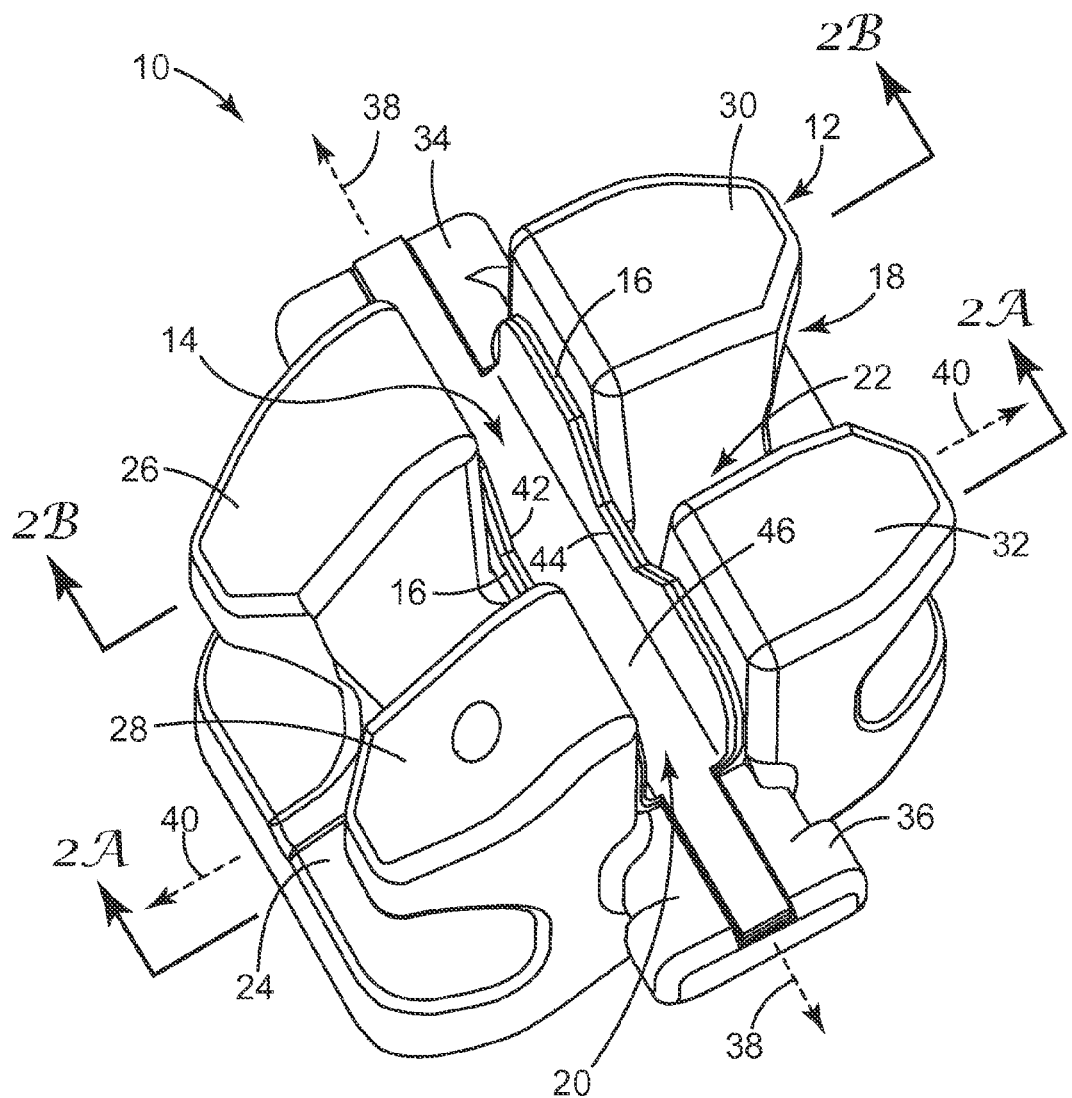
FIG. 1 is a top perspective view of an orthodontic article having an archwire slot liner disposed within an archwire slot of a ceramic bracket with an Ag—Cu—Ti brazing alloy.

FIG. 1 is a top perspective view of orthodontic article 10, which includes bracket 12, liner 14, and brazing alloy layer 16. Bracket 12 is an orthodontic bracket that includes body 18, archwire slot 20, and debonding channel 22, where body 18 includes base 24, gingival tiewings 26 and 28, occlusal tiewings 30 and 32, and posts 34 and 36. Base 24 is the portion of orthodontic article 10 that bonds to a patient's enamel tooth surface with the use of an adhesive. Gingival tiewings 26 and 28 and occlusal tiewings 30 and 32 are wing-like structures integrally formed with base 24 for retaining an archwire (not shown) within archwire slot 20. Posts 34 and 36 are respectively a mesial post and a distal post, which are integrally formed with base 24, and which extend along mesial-distal axis 38 for supporting archwire latches (not shown).

Body 18 of bracket 12 is formed from a ceramic material, which provides optically translucent properties to bracket 12. Examples of suitable ceramic materials for body 18 include monocrystalline and polycrystalline aluminum oxide materials, such as the optically-translucent ceramic materials disclosed in Kelly et al., U.S. Pat. No. 4,954,080 and Castro et al., U.S. Pat. No. 6,648,638. The ceramic material of body 18 is also a fine-grained ceramic material (i.e., a small average grain size). Examples of suitable average grain sizes for the ceramic material of body 18 include average grain sizes of about 5.0 micrometers or less, with particularly suitable average grain sizes including about 1.0 micrometer or less. The small average grain size provides strong torque strengths for bracket 12, while also preserving its optical translucence.

Archwire slot 20 is a slot extending along mesial-distal axis 38, and is generally disposed between gingival tiewing 26 and occlusal tiewing 30, and between gingival tiewing 28 and occlusal tiewing 32. As such, archwire slot 20 terminates at posts 34 and 36. Archwire slot 20 is the region of bracket 12 that retains liner 14, brazing alloy layer 16, and an archwire (not shown) during use. Debonding channel 22 is a second slot extending along occlusal-gingival axis 40, which is perpendicular to mesial-distal axis 38. Accordingly, debonding channel 22 is generally disposed between gingival tiewings 26 and 28, and between occlusal tiewings 30 and 32. Debonding channel 22 facilitates the removal of orthodontic article 10 from a patient's tooth at the conclusion of treatment, as described in Hansen, U.S. Pat. No. 5,439,379.

Liner 14 is a U-shaped, archwire slot liner that includes gingival wall 42, occlusal wall 44, and lingual wall 46, where gingival wall 42 and occlusal wall 44 are lateral walls of liner 14 integrally connected to lingual wall 46. As shown, gingival wall 42 is disposed adjacent gingival tiewings 26 and 28, and occlusal wall 42 is disposed adjacent occlusal tiewings 30 and 32. Occlusal wall 44 extends through archwire slot 20 along mesial-distal axis 38, and terminates at posts 34 and 36. In an alternative embodiment, posts 34 and 36 are omitted from body 18 of bracket 12. In this embodiment, lingual wall 46 of liner 14 only extends along mesial-distal axis 38 within archwire slot 20.

Liner 14 is secured to body 18 of bracket 12 with brazing alloy layer 16, which is a layer of an Ag—Cu—Ti brazing alloy fused to liner 14 and to body 18. Adhesion of metallic liners to ceramic materials typically require active-metal brazing alloys. However, when fine-grained ceramic articles are brazed with active-metal brazing alloys such as silver-titanium (Ag—Ti) brazing alloys, the torque strength of the resulting articles decrease, thereby reducing the strengths of the articles. In contrast, the Ag—Cu—Ti brazing alloy layer 16 provides a strong metal-to-ceramic adhesive bond between liner 14 and body 18, and substantially preserves the torque strength of bracket 12. Furthermore, brazing alloy layer 16 also provides a corrosion resistant bond, thereby preserving the adhesion between liner 14 and body 18 during use in a patient's mouth.

Figure 2A:
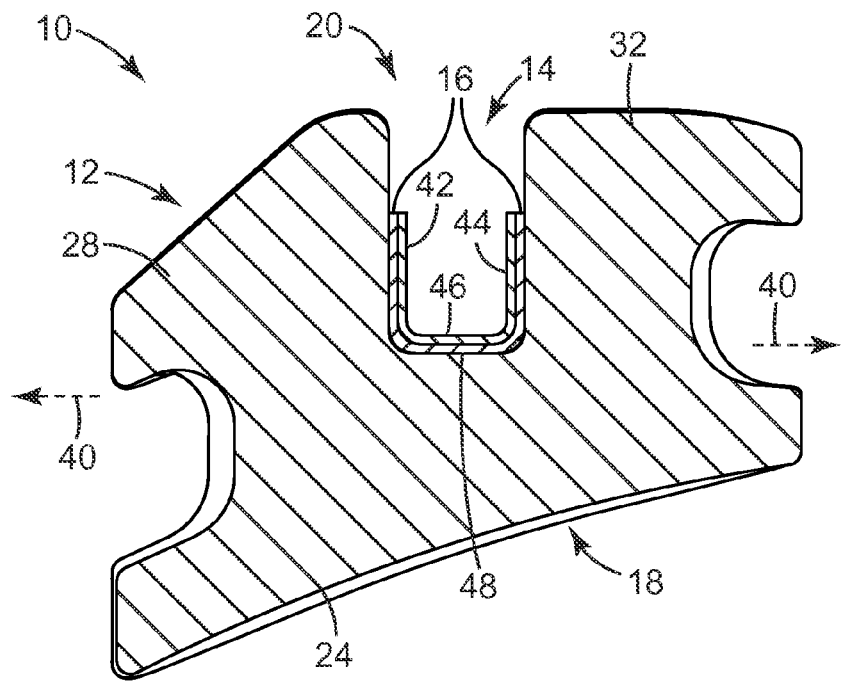
FIG. 2A is a sectional view of section 2A-2A taken in FIG. 1, showing a distal portion of the orthodontic article.
Figure 2B:
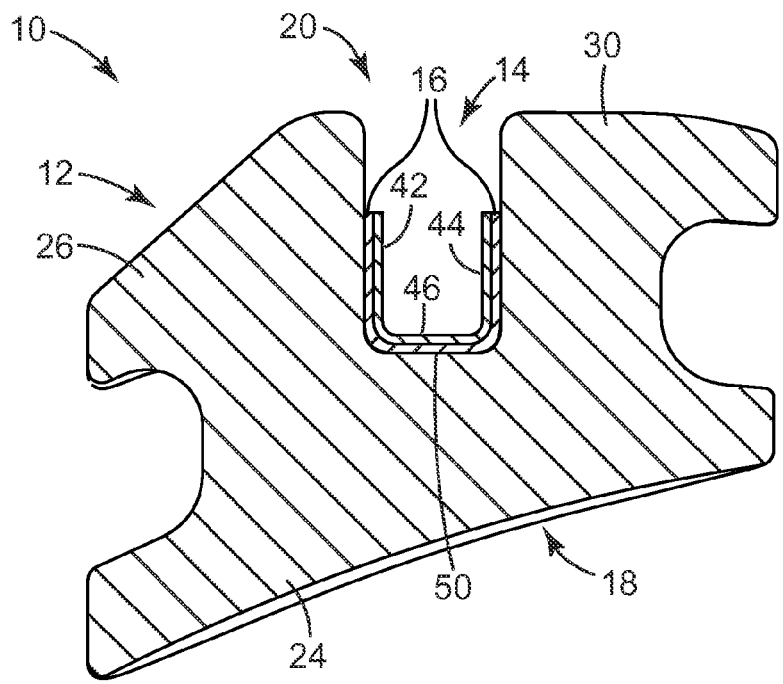
FIG. 2B is a sectional view of section 2B-2B taken in FIG. 1, showing a mesial portion of the orthodontic article.

FIGS. 2A and 2B are sectional views of respective sections 2A-2A and 2B-2B taken in FIG. 1. As shown in FIG. 2A, archwire slot 20 includes base surface 48, located between tiewings 28 and 32. As discussed above, gingival wall 42 is the portion of liner 14 that is disposed adjacent to gingival tie wing 28, and occlusal wall 44 is the portion of liner 14 that is disposed adjacent to occlusal tie wing 32. Lingual wall 46 is perpendicular to gingival wall 42 and occlusal wall 44, and is disposed adjacent to base surface 48 of archwire slot 20.

As shown in FIG. 2B, archwire slot 20 also includes base surface 50, located between tiewings 26 and 30. Liner 14 extends across debonding channel 22 (shown in FIG. 1) such that gingival wall 42 is also disposed adjacent to gingival tie wing 26, occlusal wall 44 is also disposed adjacent to occlusal tie wing 30, and lingual wall 46 is also disposed adjacent to base surface 50 of archwire slot 20.

Liner 14 is formed from a metallic material that provides sliding mechanics similar to the sliding mechanics observed with appliances that are entirely made of metallic materials. Thus, when an archwire (not shown) is retained within liner 14 and archwire slot 20, the metal-to-metal contact between the archwire and liner 14 provides good sliding mechanics (i.e., reduced galling and frictional resistance). Examples of suitable materials for the liner 14 include stainless steel, titanium, gold, alloys of cobalt and chromium, alloys of iron, nickel and chromium, and combinations thereof. Additionally, liner 14 may be plated with a metallic material (e.g., nickel plating).

Brazing alloy layer 16 is disposed between body 18 of bracket 12 and liner 14 at one or more locations between body 18 and bracket 12, thereby fusing liner 14 to the one or more locations of body 18. In one embodiment, brazing alloy layer 16 is disposed at least between lingual wall 46 of liner 14 and base surfaces 48 (shown in FIG. 2A) and 50. As such, liner 14 is fused to body 18 along the base of archwire slot 20. In this embodiment, brazing alloy layer 16 is also desirably disposed between lingual wall 46 and posts 34 and 36, thereby further securing liner 14 to body 18 of bracket 12.

In an alternative embodiment, brazing alloy layer 16 is disposed at least between gingival wall 42 of liner 14 and gingival tie wings 26 and 28 (tiewing 28 shown in FIG. 2A), and between occlusal wall 44 of liner 14 and occlusal tie wings 30 and 32 (tiewing 32 shown in FIG. 2A). This embodiment laterally fuses liner 14 to body 18 at the occlusal and gingival tiewings.

In yet another embodiment, brazing alloy layer 16 is disposed at least between gingival wall 42 of liner 14 and gingival tie wings 26 and 28, between occlusal wall 44 of liner 14 and occlusal tie wings 30 and 32, and between lingual wall 46 of liner 14 and base surfaces 48 and 50. This embodiment is a combination of the two above-discussed embodiments, and provides for a strong bond between liner 14 and body 18 of bracket 12.

Brazing alloy layer 16 is an Ag—Cu—Ti brazing alloy that at least includes silver, copper, and titanium, where the concentration of titanium in the Ag—Cu—Ti brazing alloy is at least about 1.5% by weight, based on the entire weight of the Ag—Cu—Ti brazing alloy. As discussed above, this combination of metals provides a strong metal-to-ceramic adhesive bond between liner 14 and body 18 that is corrosion resistant, and substantially preserves the torque strength of bracket 12.

Suitable maximum concentrations of titanium in the Ag—Cu—Ti brazing alloy include about 2.5% by weight (i.e., titanium concentrations ranging from about 1.5% by weight to about 2.5% by weight), with particularly suitable maximum concentrations including about 2.0% (i.e., titanium concentrations ranging from about 1.5% by weight to about 2.0% by weight), based on the entire weight of the Ag—Cu—Ti brazing alloy. Concentrations of at least about 1.5% by weight titanium in the Ag—Cu—Ti brazing alloy provide good wetting and metallurgical bonding to the ceramic material of body 18. Additionally, titanium concentrations of about 2.5% or less reduce the risk of forming cracks in the fused bond between liner 14 and body 18, and also reduce the risk of creating intergranular penetration issues.

Suitable concentrations of silver in the Ag—Cu—Ti brazing alloy range from about 60.0% by weight to about 70.0% by weight, with particularly suitable concentrations ranging from about 60.0% by weight to about 65.0% by weight, based on the entire weight of the Ag—Cu—Ti brazing alloy. Suitable concentrations of copper in the Ag—Cu—Ti brazing alloy range from about 30.0% by weight to about 40.0% by weight, with particularly suitable concentrations ranging from about 33.0% by weight to about 36.0% by weight, based on the entire weight of the Ag—Cu—Ti brazing alloy.

In one embodiment, the Ag—Cu—Ti brazing alloy of brazing alloy layer 16 also includes an additive metal material, such as tin (Sn) to provide an Ag—Cu—Ti—Sn brazing alloy. Suitable concentrations of tin in the Ag—Cu—Ti—Sn brazing alloy range from about 0.1% by weight to about 2.0% by weight, with particularly suitable concentrations ranging from about 0.5% by weight to about 1.5% by weight, based on the entire weight of the Ag—Cu—Ti—Sn brazing alloy.

Figure 3:
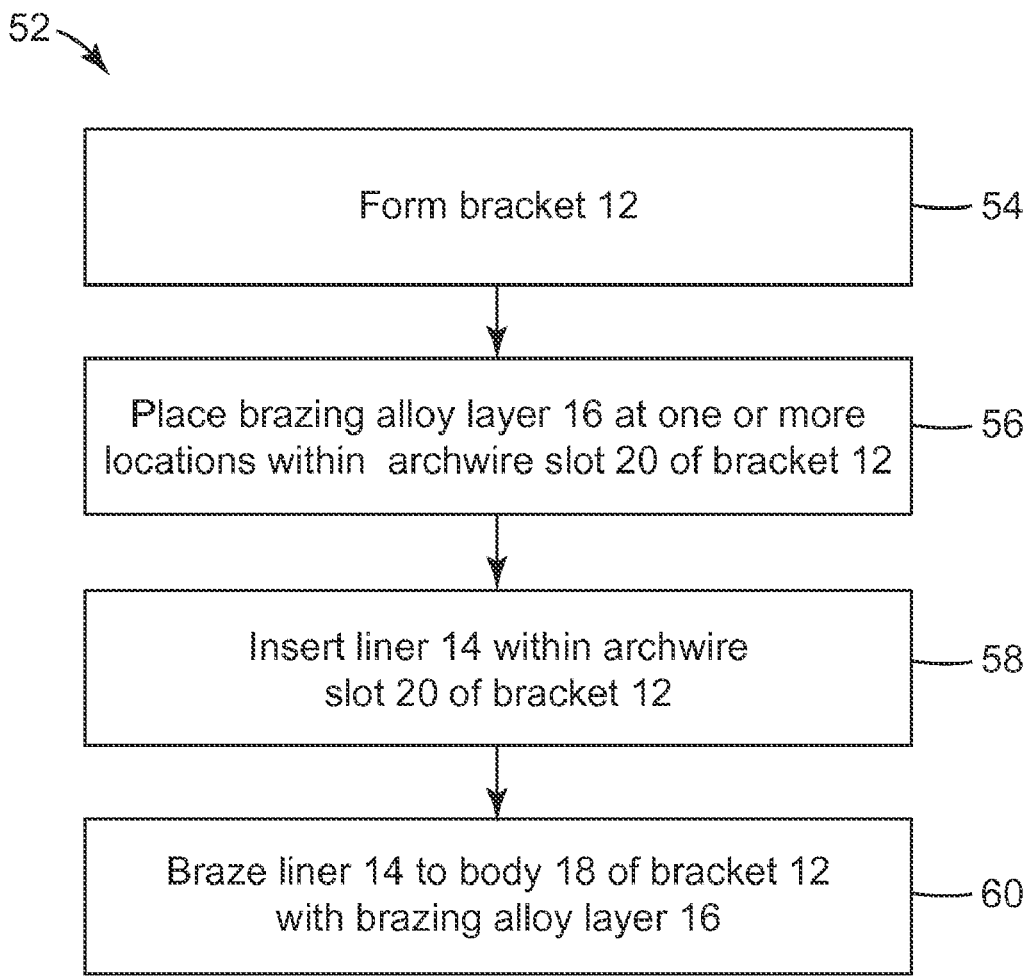
FIG. 3 is a flow diagram of a method of making the orthodontic article.

FIG. 3 is a flow diagram of method 52 for forming orthodontic article 10 with a brazing process. Method 52 includes steps 54-60, and initially involves forming bracket 12 from a fine-grain ceramic material (step 54). Bracket 12 may be formed with standard techniques for manufacturing orthodontic brackets (e.g., injection molding). Brazing alloy layer 16 is then placed at one or more locations within archwire slot 20 of bracket 12 (step 56). This may be performed in a variety of manners depending on how the Ag—Cu—Ti brazing alloy is provided. For example, the Ag—Cu—Ti brazing alloy may be provided as a thin foil that is molded or otherwise shaped to complement the dimensions of liner 14 and archwire slot 20. The thin foil of the Ag—Cu—Ti brazing alloy is then inserted into archwire slot 20. Alternatively, the Ag—Cu—Ti brazing alloy may be deposited (e.g., by physical, chemical, or plasma deposition) onto one or more surfaces of body 18 within archwire slot 20 (and/or onto posts 34 and 36), thereby forming brazing alloy layer 16.

Liner 14 is then inserted into archwire slot 20 such that brazing alloy layer 16 is disposed between liner 14 and one or more surfaces of body 18 within archwire slot 20 (step 58). In an alternative embodiment, brazing alloy layer 16 is placed on the outer walls of liner 14, and the combined liner 14/brazing alloy layer 16 is then inserted into archwire slot 20. When liner 14 and brazing alloy layer 16 are adequately positioned within archwire slot 20, liner 14 is then brazed to body 18 of bracket 12 with brazing alloy layer 16 (step 60). This involves heating orthodontic article 10 (i.e., bracket 12, liner 14, and brazing alloy layer 16) in a vacuum (e.g., less than about $1\times10^{-4}$ torr), thereby fusing the Ag—Cu—Ti brazing alloy of brazing alloy layer 16 to the metal of liner 14 and to the ceramic material of body 18.

A suitable heating profile for the brazing process includes heating bracket 12, liner 14, and brazing alloy layer 16 at an incremental rate (e.g., 5° C./minute) until an equilibration temperature is obtained. Suitable equilibration temperatures range from about 725° C. to about 775° C. The temperature is then maintained at the equilibration temperature for a sufficient amount of time to equilibrate the temperatures of bracket 12, liner 14, and brazing alloy layer 16 (e.g., about 5-30 minutes). The temperature is then increased at an incremental rate (e.g., 5° C./minute) until a brazing temperature of the Ag—Cu—Ti brazing alloy is reached. Examples of suitable brazing temperatures for the Ag—Cu—Ti brazing alloy range from about 800° C. to about 850° C., with particularly suitable brazing temperatures ranging from about 810° C. to about 830° C. The temperature is then maintained at the brazing temperature for a time period ranging from about 5 to about 20 minutes.

After the brazing period, orthodontic article 10 is then cooled at a rapid incremental rate (e.g., about 10° C./minute) until the equilibrium temperature is reached. The cooling rate is then reduced (e.g., about 5° C./minute) until an intermediate temperature is reached (e.g., about 600° C. to about 650° C.). The temperature is desirably held at the intermediate temperature for a sufficient period of time to relieve heat-induced stresses before cooling orthodontic article 10 down to room temperature. The resulting orthodontic article 10 then includes liner 14 fused to body 18, within archwire slot 20, with brazing alloy layer 16. This provides a strong metal-to-ceramic adhesive bond between line 14 and body 18 that is corrosion resistant, and which substantially preserves the torque strength of bracket 12.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Orthodontic articles of Example 1 and Comparative Examples A-F were each prepared and evaluated for torque strengths pursuant to the following procedures:

Comparative Example A

The article of Comparative Example A was a fine-grain ceramic bracket having dimensions similar to the dimensions of bracket 12 (shown in FIG. 1), except that the article of Comparative Example A did not include an archwire slot liner or brazing alloy layer. The fine-grain ceramic bracket was injection-molded from an aluminum oxide ($Al_2O_3$) material, and had an average grain size of less than 1.0 micrometer.

Example 1

The article of Example 1 included a metal archwire slot liner fused to a fine-grain ceramic bracket with an Ag—Cu—Ti—Sn brazing alloy. The fine-grain ceramic bracket used was the same as discussed above for Comparative Example A. The metal archwire slot liner was a nickel-plated stainless-steel foil fabricated into the shape of an archwire slot liner. The Ag—Cu—Ti—Sn brazing alloy was a braze foil that compositionally included 63.00% silver, 34.25% copper, 1.75% titanium, and 1.00% tin, and was commercially available under the trade designation "CUSIN-1-ABA" from Wesgo Metals, a division of Morgan Advanced Ceramics, Hayward, Calif.

The Ag—Cu—Ti—Sn brazing alloy was inserted onto the metal archwire slot liner, and the combined liner/brazing alloy was inserted into the archwire slot of the bracket such that the Ag—Cu—Ti—Sn brazing alloy was disposed between the bracket and the occlusal wall, the gingival wall, and the lingual wall of the liner. The article was then brazed in a vacuum furnace by Ceradyne, Inc., Coast Mesa, Calif., using standard brazing temperatures and time profiles. This caused the liner to fuse to the body of the bracket with the Ag—Cu—Ti—Sn brazing alloy, thereby forming the article of Example 1.

Comparative Example B

The article of Comparative Example B was similar to the article of Example 1, except that a silver-titanium (Ag—Ti) brazing alloy was used in lieu of the Ag—Cu—Ti—Sn brazing alloy. The Ag—Ti brazing alloy was a braze foil that compositionally included 97.0% silver and 3.0% titanium, and was commercially available under the trade designation "CB2" from Umicore-BrazeTec GmbH, Hanau, Germany. The article of Comparative Example B was brazed pursuant to the procedure discussed above for the article of Example 1.

Comparative Example C

The article of Comparative Example C was similar to the bracket of Comparative Example B, except that a coarse-grain ceramic bracket was used in lieu of the fine-grain bracket. The coarse-grain ceramic bracket was a trade designated "CLARITY" ceramic bracket (available from 3M Unitek Corporation, Monrovia, Calif.), which included an aluminum oxide material (commercially available under the trade designation "TRANSTAR" from Ceradyne, Inc., Coast Mesa, Calif.), and which had grain sizes ranging from 10-30 micrometers.

Comparative Examples D-F

Torque test results for the articles of Comparative Examples D-F were obtained from reported results of a braze post-process test from Ceradyne, Inc., Coast Mesa, Calif. The articles of Comparative Examples D-F each included the fine-grain ceramic bracket and the liner as discussed above for the article of Example 1, and were brazed in the same manner. The article of Comparative Example D used a brazing alloy that included 82.00% gold, 16.00% nickel, 1.25% vanadium, and 0.25% molybdenum (i.e., an Au—Ni—V—Mo brazing alloy), which was commercially available from Wesgo Metals, a division of Morgan Advanced Ceramics, Hayward, Calif. The article of Comparative Example E used a brazing alloy that included 98.4% silver, 1.0% indium, and 0.6% titanium (i.e., an Ag—In—Ti brazing alloy), which was commercially available from Umicore-BrazeTec GmbH, Hanau, Germany. The article of Comparative Example F used a brazing alloy that included 59.00% silver, 27.25% copper, 12.50% indium, and 1.25% titanium (i.e., an Ag—Cu—In—Ti brazing alloy), which was commercially available from Wesgo Metals.

Table 1 provides a summary of the brackets and brazing alloy layers used for each of the orthodontic articles of Example 1 and Comparative Examples A-F.

TABLE 1

| Example | Bracket | Brazing Alloy |
|---|---|---|
| Example 1 | Fine-grain bracket | Ag—Cu—Ti—Sn alloy (1.75% Ti) |
| Comparative Example A | Fine-grain bracket | None |
| Comparative Example B | Fine-grain bracket | Ag—Ti alloy (3.0% Ti) |
| Comparative Example C | Coarse-grain bracket | Ag—Ti alloy (3.0% Ti) |
| Comparative Example D | Fine-grain bracket | Au—Ni—V—Mo alloy |
| Comparative Example E | Fine-grain bracket | Ag—In—Ti alloy (0.6% Ti) |
| Comparative Example F | Fine-grain bracket | Ag—Cu—In—Ti alloy (1.25% Ti) |

The torque strengths of the articles of Example 1 and Comparative Examples A-C were then each quantitatively and qualitatively measured using an apparatus and method adapted from Holt, M. H. et al., "Fracture Resistance of Ceramic Brackets During Arch Wire Torsion," AJO-DO, 99 (4), April 1991, pp. 287-293. In the test, torsion was applied from one side of the bracket, where the torsion load was focused on one pair of tiewings rather than all four tiewings at once.

Each bracket had 0° torque, 8° angulation, and 0° rotation with nominally 0.56 millimeter (mm) (22 mil) archwire slots. For each condition, a set of 5 brackets was bonded to the convex perimeter of a knurled stainless steel ring. Each bracket of the set was oriented such that the archwire slot was parallel to the center axis of the ring and centered in the mesial-distal direction, and such that the torque in the archwire slot would face the draw chain. Bonding took place by applying about 10 milligrams of an orthodontic adhesive to the base of each bracket, then fully seating each bracket onto the knurled ring surface. The orthodontic adhesive was a light-curable adhesive commercially available under the trade designation "TRANSBOND XT" from 3M Company, St. Paul, Minn. Excess adhesive was removed from the edges of the bracket base using a scalar or similar hand instrument. Finally, the adhesive was cured by irradiation through the bracket at close range (less than 0.5 centimeters) using a curing light for five seconds per bracket. The curing light was a light-curing unit commercially available under the trade designation "ORTHOLUX LED" from 3M Company, St. Paul, Minn. Following irradiation, the brackets of the set were allowed to sit at room temperature for 24 hours.

The torque test was performed on each mounted bracket of the set by raising the bracket until a Standard Permachrome archwire (0.546 mm×0.711 mm) was seated flat into the archwire slot. The ring holder screw was then tightened, and then the riser screw was tightened. Using a crosshead speed of 5.1 centimeters/minute (2.0 inches/minute), torque was applied to the bracket until bracket failure occurred. The test was then stopped, and the curves analyzed to determine the maximum torque, or torque strength. The archwire was replaced after testing each bracket. This procedure was repeated for each mounted bracket of the set and the overall torque strength value reported as the average of these replicated measurements.

As discussed above, the torque strengths of the brackets of Comparative Examples D-F were obtained from the braze post-process test results performed by Ceradyne, Inc., Coast Mesa, Calif., and are believed to be reliable comparative values. Table 2 lists the resulting average torque strengths and qualitative comments for the articles of Example 1 and Comparative Examples A-F. The average torque strengths were based on five test runs, except for the bracket of Comparative Example A, which was tested 58 times to obtain a baseline value and standard deviation of the non-brazed bracket. Additionally, the article of Example 1 was tested in duplicate (i.e., Examples 1a and 1b).

TABLE 2

| Example | Torque Strength (N-cm) | Torque Strength (inch-ounce) | Qualitative Comments |
|---|---|---|---|
| Example 1a | 8.1 | 11.4 | Brazed, wetted, and held together during the torque test |
| Example 1b | 7.7 | 10.9 | Had some voids, but brazed, wetted, and held together during torque test |
| Comparative Example A | 6.5 ± 0.9 | 9.3 ± 1.2 | N/A |
| Comparative Example B | 4.4 | 6.2 | Brazed, wetted, and held together during the torque test |
| Comparative Example C | 6.5 | 9.2 | Brazed, wetted, and held together during the torque test |
| Comparative Example D | 4.7 | 6.7 | Did not braze or wet |
| Comparative Example E | 5.2 | 7.4 | Did not hold together during the torque test |
| Comparative Example F | 4.1 | 5.8 | Did not wet, and did not hold together during the torque test |

The results shown in Table 2 illustrate how the brazing processes affected the torque strengths of the articles of Examples 1 and Comparative Examples B-F. A comparison of Comparative Examples A and B show that the brazing process decreased the torque strength of the bracket when the Ag—Ti brazing alloy was used. In contrast, the torque strengths of the brackets of Examples 1a and 1b were greater than those of the article of Comparative Example A. As such, the use of the Ag—Cu—Ti—Sn brazing alloy layers increased the strengths of the articles of Examples 1a and 1b.

Additionally, with respect to the articles of Comparative Examples D-F, the brazing alloys did not wet and/or did not hold the liner and the bracket together during the torque test. In particular, the low concentrations of titanium in the brazing alloys in the articles of Comparative Examples E and F (i.e., 0.6% and 1.25%, respectively) were not sufficient to provide suitable bond strengths between the liners and the brackets. In contrast, the concentration of titanium in the brazing alloy used in the articles of Examples 1a and 1b (i.e., 1.75%) provided strong bonds that held the liners to the brackets during the torque tests. Accordingly, as discussed above, titanium concentrations of at least about 1.5% in the brazing alloy are believed to provide suitable bonds between the liner and the fine-grain ceramic bracket.

The orthodontic articles of Example 1b and Comparative Examples B and C were also each subjected to corrosive conditions and retested for torque strengths to measure the corrosion resistance of the given brazing alloys. The corrosive conditions involved exposing each bracket to Ringer's solution at 75° C. for 24 hours. Table 3 provides the resulting average torque strengths and qualitative comments for the articles of Example 1b and Comparative Examples B and C, after being subjected to the corrosive conditions. The average torque strengths were based on five test runs.

TABLE 3

| Example | Torque Strength (N-cm) | Torque Strength (inch-ounce) | Qualitative Comments |
|---|---|---|---|
| Example 1b | 7.4 | 10.5 | Had some voids, but brazed, wetted, and held together during torque test |
| Comparative Example B | 4.2 | 6.0 | Brazed, wetted, and some fell apart during the torque test |
| Comparative Example C | 5.7 | 8.0 | Brazed, wetted, and some fell apart during the torque test |

The results shown in Table 3 illustrate the corrosion resistance exhibited by the article of Example 1b. Even after being subjected to the corrosive conditions, the article of Example 1b substantially retained its post-brazing torque strength. In contrast, after being subjected to the corrosive conditions, some of the tested articles of Comparative Examples B and C fell apart during the torque test. Furthermore, the torque strength of the article of Comparative Example C decreased after being subjected to the corrosive conditions.

Accordingly, the article of Example 1, which includes a fine-grain ceramic bracket and a liner secured within the archwire slot of the bracket with an Ag—Cu—Ti—Sn brazing alloy, provides torque strengths that are at least as high as the pre-brazed bracket and corrosion resistant bonds. As a result, the article of Example 1 is capable of retaining the liner to the bracket during use in oral environments.

Although the present invention has been described with reference to preferred embodiments, workers skilled in the art will recognize that changes may be made in form and detail without departing from the spirit and scope of the invention.

The invention claimed is:

1. An orthodontic article comprising:
    a bracket having an archwire slot, and compositionally comprising a ceramic material having an average grain size of about 5.0 micrometers or less; and
    a metal liner secured in the archwire slot with a brazing alloy comprising silver, copper, and at least about 1.5% by weight titanium, based on an entire weight of the brazing alloy.

2. The orthodontic article of claim 1, wherein the average grain size of the ceramic material is about 1.0 micrometer or less.

3. The orthodontic article of claim 1, wherein the titanium constitutes about 1.5% by weight to about 2.5% by weight of the brazing alloy, based on the entire weight of the brazing alloy.

4. The orthodontic article of claim 3, wherein the titanium constitutes about 1.5% by weight to about 2.0% by weight of the brazing alloy, based on the entire weight of the brazing alloy.

5. The orthodontic article of claim 1, wherein the silver constitutes about 60.0% by weight to about 70.0% by weight of the brazing alloy, based on the entire weight of the brazing alloy.

6. The orthodontic article of claim 1, wherein the copper constitutes about 30.0% by weight to about 40.0% by weight of the brazing alloy, based on the entire weight of the brazing alloy.

7. The orthodontic article of claim 1, wherein the brazing alloy further comprises tin.

8. The orthodontic article of claim 7, wherein the tin constitutes about 0.1% by weight to about 2.0% by weight of the brazing alloy, based on the entire weight of the brazing alloy.

9. An orthodontic article comprising:
    a bracket having a body defining an archwire slot, and compositionally comprising a ceramic material having an average grain size of about 5.0 micrometers or less;
    a metal liner disposed in the archwire slot, the metal liner having an occlusal wall, a gingival wall, and a lingual wall interconnecting the occlusal wall and the gingival wall; and
    an Ag—Cu—Ti brazing alloy disposed in the archwire slot between the body of the bracket and at least one of the occlusal wall, the gingival wall, and the lingual wall of the metal liner, the Ag—Cu—Ti brazing alloy having a titanium concentration of at least about 1.5% by weight, based on an entire weight of the brazing alloy.

10. The orthodontic article of claim 9, wherein the average grain size of the ceramic material is about 1.0 micrometer or less.

11. The orthodontic article of claim 9, wherein the titanium concentration constitutes about 1.5% by weight to about 2.5% by weight of the Ag—Cu—Ti brazing alloy, based on the entire weight of the Ag—Cu—Ti brazing alloy.

12. The orthodontic article of claim 11, wherein the titanium concentration constitutes about 1.5% by weight to about 2.0% by weight of the Ag—Cu—Ti brazing alloy, based on the entire weight of the Ag—Cu—Ti brazing alloy.

13. The orthodontic article of claim 9, wherein the Ag—Cu—Ti brazing alloy comprises an Ag—Cu—Ti—Sn brazing alloy.

14. The orthodontic article of claim 9, wherein the Ag—Cu—Ti brazing alloy is disposed within the archwire slot between the body of the bracket and the occlusal wall, the gingival wall, and the lingual wall of the metal liner.

15. A method of making an orthodontic article, the method comprising:
    providing a bracket having a body defining an archwire slot, and compositionally comprising a ceramic material having an average grain size of about 5.0 micrometers or less;
    placing a brazing alloy layer within the archwire slot, the brazing alloy layer being formed from a brazing alloy comprising silver, copper, and at least about 1.5% by weight titanium, based on an entire weight of the brazing alloy;
    inserting a metal liner within the archwire slot such that the brazing alloy layer is disposed between the metal liner and at least one surface of the body of the bracket; and
    brazing the metal liner to the at least one surface of the body with the brazing alloy.

16. The method of claim 15, wherein the average grain size of the ceramic material is about 1.0 micrometer or less.

17. The method of claim 15, wherein the titanium constitutes about 1.5% by weight to about 2.5% by weight of the brazing alloy, based on the entire weight of the brazing alloy.

18. The method of claim 17, wherein the titanium constitutes about 1.5% by weight to about 2.0% by weight of the brazing alloy, based on the entire weight of the brazing alloy.

19. The method of claim 15, wherein the brazing alloy further comprises tin.

20. The method of claim 15, wherein brazing the metal liner to the at least one surface of the body with the brazing alloy comprises heating the bracket, the brazing alloy layer, and the metal part to a temperature ranging from about 800° C. to about 850° C.

* * * * *